(12) United States Patent
Ahn et al.

(10) Patent No.: US 12,016,965 B2
(45) Date of Patent: Jun. 25, 2024

(54) AUTOMATIC SUPPLYING DEVICE FOR MEDICAL CLEANING AGENT

(71) Applicants: Byung Moon Ahn, Seoul (KR); Jin Ki Ahn, Seoul (KR)

(72) Inventors: Byung Moon Ahn, Seoul (KR); Jin Ki Ahn, Seoul (KR)

( * ) Notice: Subject to any disclaimer, the term of this patent is extended or adjusted under 35 U.S.C. 154(b) by 553 days.

(21) Appl. No.: 17/339,656

(22) Filed: Jun. 4, 2021

(65) Prior Publication Data

US 2021/0386895 A1 Dec. 16, 2021

(30) Foreign Application Priority Data

Jun. 15, 2020 (KR) .......................... 10-2020-0072370

(51) Int. Cl.
  *A61L 2/24* (2006.01)
  *A61B 90/70* (2016.01)
  *A61L 2/18* (2006.01)

(52) U.S. Cl.
  CPC ................ *A61L 2/24* (2013.01); *A61B 90/70* (2016.02); *A61L 2/18* (2013.01); *A61L 2202/122* (2013.01); *A61L 2202/14* (2013.01); *A61L 2202/15* (2013.01); *A61L 2202/24* (2013.01)

(58) Field of Classification Search
  CPC ..... A61B 90/70; A61B 2090/701; A61L 2/18; A61L 2202/15; A61L 2202/24
  See application file for complete search history.

(56) References Cited

U.S. PATENT DOCUMENTS

2014/0010675 A1* 1/2014 Kent ..................... F04B 43/009
                                                                        417/476

* cited by examiner

*Primary Examiner* — Sean E Conley
*Assistant Examiner* — Justin Hwang
(74) *Attorney, Agent, or Firm* — John K. Park; PARK LAW FIRM

(57) ABSTRACT

The present invention relates to an automatic medical device cleaning agent supply device, comprising a case, peristaltic pump unit, timer unit, foot switch, and controller, that automatically supplies the cleaning solution into the cleaning tank to clean medical devices in an amount relative to the amount of water in the cleaning tank when the foot switch is pressed and wherein an attachment housing is secured on a fixed housing in the peristaltic pump unit in a detachable manner for the attachment housing to be selectively detached to facilitate tube replacement and use, through which the tube, which is a consumable, can be replaced conveniently to ensure the ease of maintenance of the device.

4 Claims, 4 Drawing Sheets

AUTOMATIC SUPPLYING DEVICE FOR MEDICAL CLEANING AGENT

BACKGROUND

1. Field of the Invention

The present invention relates to an automatic medical device cleaning agent supply device, more specifically an automatic medical device cleaning agent supply device which comprises a case, peristaltic pump unit, timer unit, foot switch, and controller, that automatically supplies the cleaning solution into the cleaning tank to clean medical devices in an amount relative to the amount of water in the cleaning tank when the foot switch is pressed and wherein an attachment housing is secured on a fixed housing in the peristaltic pump unit in a detachable manner for the attachment housing to be selectively detached to facilitate tube replacement and use, through which the tube, which is a consumable, can be replaced conveniently to ensure the ease of maintenance of the device.

2. Discussion of Related Art

Generally, a peristaltic pump is a type of pump that transports fluid inside a tube by exerting pressure on an elastic tube in a certain direction.

Such peristaltic pumps do not require special parts and components for maintaining airtightness, such as O-rings and gaskets, which are essential in other fluid pumps.

Peristaltic roller pumps, as described above, are applied to technical fields such as mechanical engineering, fluid mechanics, pumps (industrial, medical, etc.), pharmaceuticals, food, and medical devices.

The transported fluid may be sealed inside the tube of the peristaltic pump, and since the fluid does not come into contact with the mechanical parts, other than the tube, peristaltic pumps are widely used in fields requiring excellent sanitation and sterilization/disinfection such as food, pharmaceuticals, and medical fields.

Moreover, for medical devices requiring sterilization/disinfection or for cleaning medical devices, peristaltic pumps have been widely used for injecting or transporting blood, fluid, and chemical or for supplying a liquid detergent to the cleaning tank for cleaning medical devices.

On the other hand, to supply the cleaning solution to the cleaning tank for cleaning medical devices, as described above, the cleaning solution was mixed with the water in the cleaning tank while pouring the cleaning solution into the cleaning tank manually.

However, the conventional method of supplying a cleaning solution to clean medical devices, as described above, presented a problem in that it was difficult to input a certain amount of the cleaning solution in relation to the amount of water in the cleaning tank, as the process was performed manually.

Therefore, there is a need to conduct research to develop an automatic medical device cleaning agent supply device that can supply a cleaning agent in an amount relative to the amount of water in the cleaning tank in an easy and automatic way when the cleaning solution is to be supplied to the cleaning tank for cleaning medical devices.

SUMMARY OF THE INVENTION

In order to address the above issues, the object of the present invention is to provide an automatic medical device cleaning agent supply device comprising a case, peristaltic pump unit, timer unit, foot switch, and controller that can supply a cleaning agent in an amount relative to the amount of water in the cleaning tank in an easy and automatic way when the cleaning solution is to be supplied to the cleaning tank for cleaning medical devices simply with the pressing and lifting movements of the foot.

Another object of the art according to the present invention is to include a case, peristaltic pump unit, timer unit, foot switch and controller, provided that a structure wherein an attachment housing is secured on a fixed housing in the peristaltic pump unit in a detachable manner for the attachment housing to be selectively detached to facilitate tube replacement and use, through which the tube, which is a consumable, can be replaced conveniently to ensure the ease of maintenance of the device.

The present invention for achieving the above object is as follows: That is, an automatic medical device cleaning agent supply device according to the present invention comprises a case, wherein suction tubing and discharge tubing that are connected and installed to suction the cleaning solution from the cleaning solution tank via the suction tubing and automatically supply a certain amount of the cleaning solution over a certain amount of time to a cleaning tank containing a certain amount of water via the discharge tubing, wherein an open top is enclosed by a cover, which comprises a power connector and a switch connection jack on one side of the bottom to be supplied power from an external source and operate the device at certain intervals, and wherein an on/off switch is installed in the center of the bottom side of the front of the cover; a peristaltic pump unit that is installed inside said case from the outside of one side of the front of said cover, to which the suction tubing is connected on one side of the bottom exposed externally, to which the discharge tubing is connected on the other side of the bottom, and which suctions the cleaning solution from the cleaning solution tank via the suction tubing as a result of rotational operation and discharges a certain amount of the cleaning solution over a certain amount of time into the cleaning tank via the discharge tubing; a timer unit, which is installed on top of the on/off switch with respect to the front side of said cover and operates for a preset amount of time in relation to the operation of the peristaltic pump unit to have a certain amount of the cleaning solution be discharged into the cleaning tank over a certain amount time; a foot switch, which is selectively connected to the switch connection jack installed in said case, wherein a peristaltic pump unit is selectively operated with the pressing and lifting movements of the foot, and which discharges a certain amount of the cleaning solution over a certain amount of time preset using the timer unit; and a controller for controlling the operation of said peristaltic pump unit, timer unit, and foot switch unit that is installed inside said case.

Here, it is desirable for said peristaltic pump unit to comprise a fixed housing that is fixed in place on one side of the front of the cover; an attachment housing that is attached and fixed to the front part of the fixed housing; a motor, which is fixed in place inside the case and to which a connector is connected to the axial tip, with the connector passing through the front of the cover and placed at the center inside the fixed housing; a rotary pressure wheel provided as a wheel type of a certain diameter, wherein multiple pressure rollers are fixed in place on the outer surface at regular intervals along the circumference and which are connected by the coupling of protruding and hole parts for the wheel to rotate with the connector, the central part on the back side of which is connected to the axial tip of the motor; a tube connected to the suction tubing connection nipple and discharge tubing connection nipple installed for one end and the other end to pass through the bottom of the fixed housing and the attachment housing on one side and the other side, while enclosing the outer circumference of said pressure wheel, that suctions the cleaning solution via the suction tubing connected to the suction tubing connection nipple to be discharged via the discharge tubing connected to the discharge tubing connection nipple.

At this time, it is preferable for said fixed housing to be penetrated with attachment holes on both sides of the front for the attachment housing to be attached to the front of said fixed housing in a detachable manner and for said attachment housing to have attachment hooks protruding outward that undergo changes in and restoration of form with tension to selectively attach to the attachment holes of said fixed housing on both sides of the edges on the back.

Also, it is desirable for said on/off switch to be provided as a round button type enabling distinction when it is pressed on and to come with strip-type LED lamps along the circumference of the button area that turn on when the switch is turned on.

Moreover, it is preferable for said foot switch to comprise a switch connection jack and a connection jack wherein the male and female are applied in alternation for interconnection on one end of the power cable and to be characterized by the inclusion of.

In addition, it is desirable for said timer unit to be provided as an analog type wherein the operating time is set by manipulating a dial.

Of course, said timer unit may be provided as a digital type wherein the operating time is set by touching the buttons on a display.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

Hereinafter, a preferred embodiment of an automatic medical device cleaning agent supply device according to the present invention will be described in detail with reference to the accompanying drawings.

Figure 1:
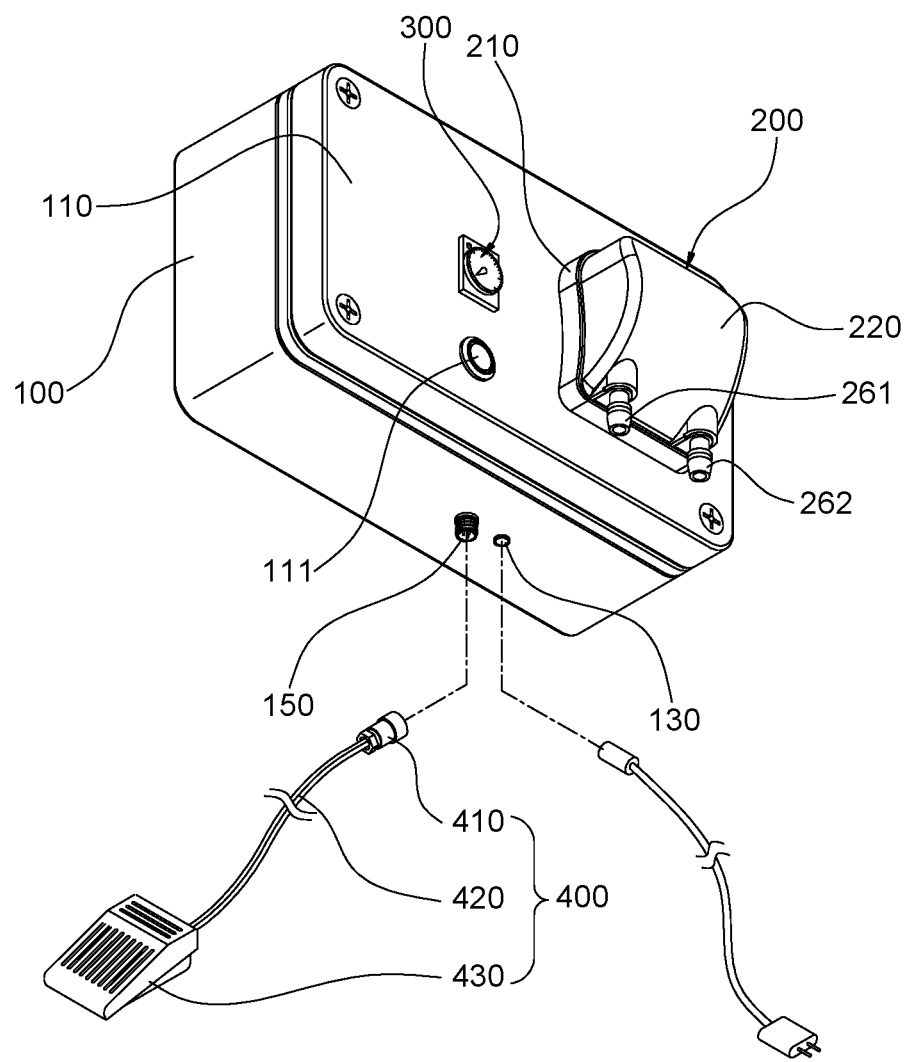
FIG. 1 is a perspective view of an automatic medical device cleaning agent supply device according to the present invention.
Figure 2:
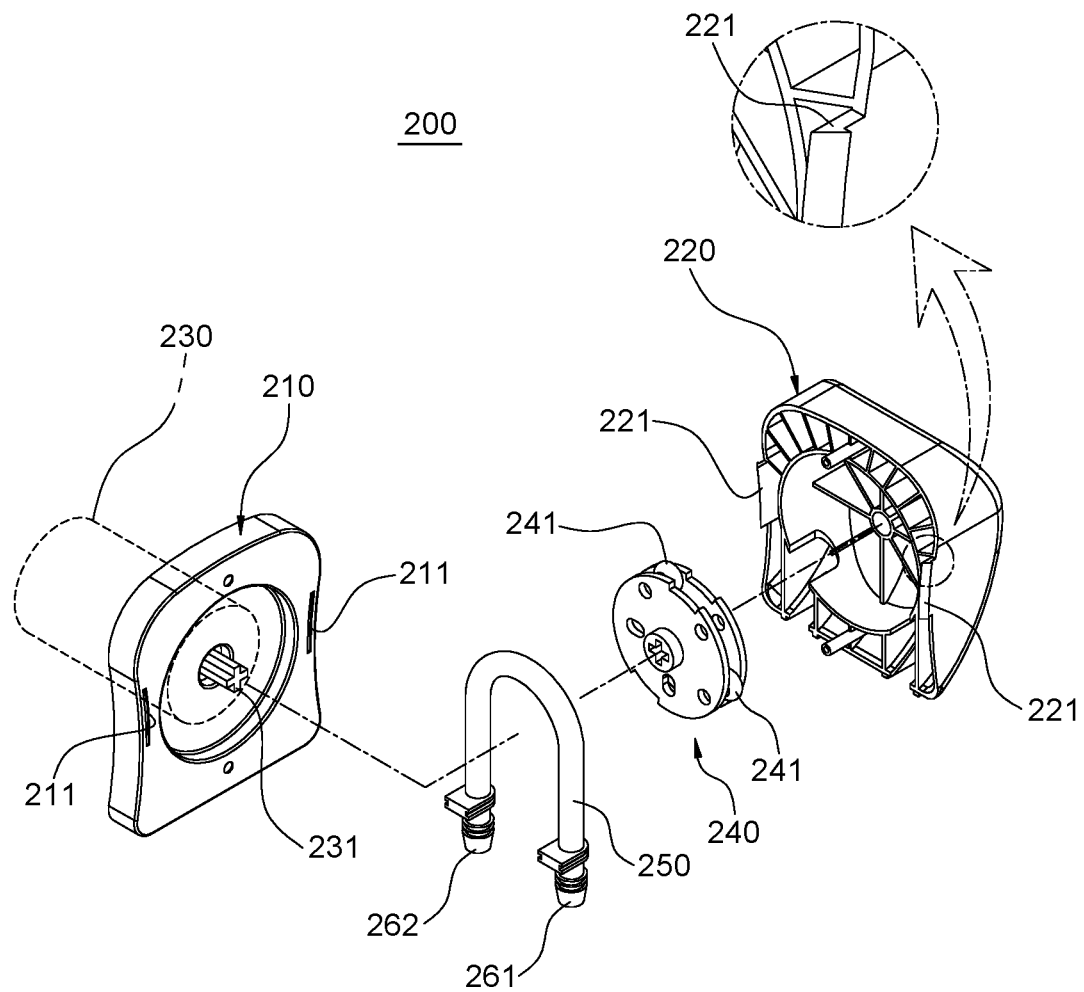
FIG. 2 is a perspective view of a device part separate from the whole showing the installation layout of a peristaltic pump unit, the part of an automatic medical device cleaning agent supply device according to the present invention.
Figure 3:
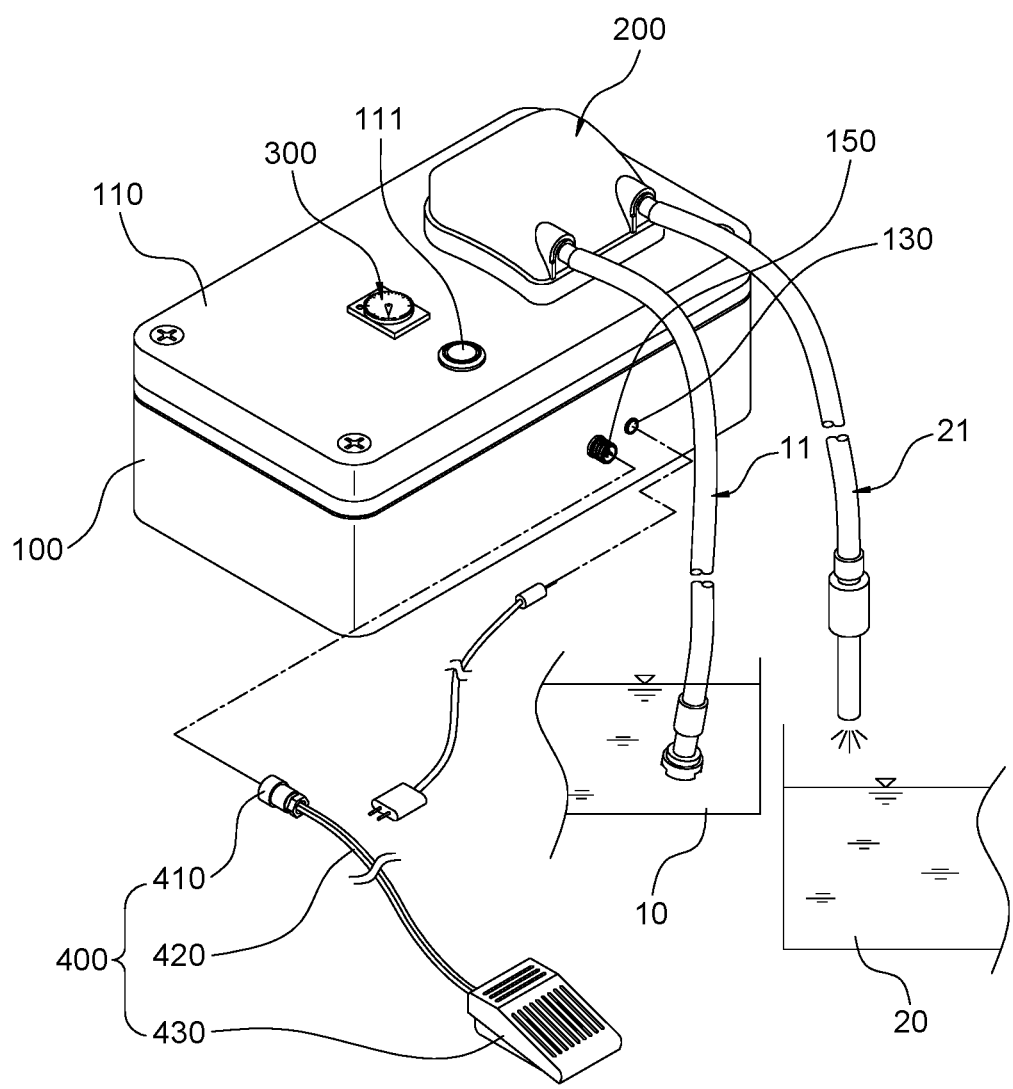
FIG. 3 is a drawing of an embodiment of an automatic medical device cleaning agent supply device according to the present invention being used to supply an automatically configured amount of a cleaning agent from a cleaning solution tank into a cleaning thank over a certain amount of time.

FIG. 1 is a perspective view of an automatic medical device cleaning agent supply device according to the present invention; FIG. 2 is a perspective view of a device part separate from the whole showing the installation layout of a peristaltic pump unit, the part of an automatic medical device cleaning agent supply device according to the present invention; FIG. 3 is a drawing of an embodiment of an automatic medical device cleaning agent supply device according to the present invention being used to supply an automatically configured amount of a cleaning agent from a cleaning solution tank into a cleaning thank over a certain amount of time.

As shown in FIGS. 1 to 3, an automatic medical device cleaning agent supply device according to a preferable embodiment of the present invention is a device wherein suction tubing (11) and discharge tubing (21) that are connected and installed to suction the cleaning solution from the cleaning solution tank (10) via the suction tubing and automatically supply a certain amount of the cleaning solution over a certain amount of time to a cleaning tank containing a certain amount of water via the discharge tubing so that it can supply a cleaning agent in relation to the amount of water in the cleaning tank in an easy and automatic way when the cleaning solution is to be supplied to the cleaning tank for cleaning medical devices.

Referring to FIGS. 1 to 3, an automatic medical device cleaning agent supply device according to the present invention, as described above, comprises a case (100), peristaltic pump unit (200), timer unit (300), foot switch (400), and controller (not shown in the drawings).

More specifically, said case (100) has an open top enclosed by a cover (110), equipped with a power connector (130) and a switch connection jack (150) on one side of the bottom to be supplied power from an external source and operate the device at certain intervals and has an on/off switch (111) installed in the center of the bottom side of the front of the cover (110).

Also, said peristaltic pump unit (200) is installed inside said case (100) from the outside of one side of the front of said cover (110), with suction tubing (11) connected on one side of the bottom exposed externally and discharge tubing (21) connected on the other side of the bottom, and suctions the cleaning solution from the cleaning solution tank (10) via the suction tubing (11) as a result of rotational operation and discharges a certain amount of the cleaning solution over a certain amount of time into the cleaning tank (20) via the discharge tubing (21).

In addition, said timer unit (300) is installed on top of the on/off switch (111) with respect to the front side of said cover (110) and operates for a preset amount of time in relation to the operation of the peristaltic pump unit (200) to have a certain amount of the cleaning solution be discharged into the cleaning tank (20) over a certain amount time.

It is desirable for a timer unit (300), as described above, to be provided as an analog type wherein the operating time is set by manipulating a dial.

Meanwhile, said foot switch (400) is selectively connected to the switch connection jack (150) installed in said case (100) and a peristaltic pump unit (200) is selectively operated with the pressing and lifting movements of the foot, provided that it discharges a certain amount of the cleaning solution over a certain amount of time preset using the timer unit (300).

Also, said controller (not shown in the drawings) is not shown specifically in the drawings, but it controls the operation of said peristaltic pump unit (200), timer unit (300), and foot switch unit (400) that is installed inside said case (100), and it is desirable for it to be installed as a structure containing a print circuit board inside said case (100).

In an automatic medical device cleaning agent supply device according to the present invention, comprising components described above, said peristaltic pump unit (200) comprises a fixed housing (210), attachment housing (220), motor (230), rotary pressure wheel (240), and tube (250).

In detail, said fixed housing (210) is fixed on one side of the front of the cover (110) and said attachment housing (220) is attached to the front of said fixed housing (210) that is open.

Also, said motor (230) fixed in place inside a case (100) has a connector (233) connected to the axial tip, with the connector (231) passing through the front of the cover (110) and placed at the center inside the fixed housing (210).

Moreover, said rotary pressure wheel (240) is provided as a wheel type of a certain diameter with multiple pressure rollers (241) are fixed in place on the outer surface at regular intervals along the circumference and is connected by the coupling of protruding and hole parts for the wheel to rotate with the connector (233), the central part on the back side of which is connected to the axial tip of the motor (230).

Also, said tube (250) is connected to the suction tubing connection nipple (261) and discharge tubing connection nipple (262) installed for one end and the other end to pass through the bottom of the fixed housing (210) and the attachment housing (220) on one side and the other side, while enclosing the outer circumference of said pressure wheel (240).

A tube (250), described as above, suctions the cleaning solution via the suction tubing (11) connected to the suction tubing connection nipple (261) to be discharged via the discharge tubing (21) connected to the discharge tubing connection nipple (262).

It is important for a peristaltic pump unit (200) comprising components described above to have an attachment housing (220) attached to the front of said fixed housing (210) that is open in a detachable manner.

To this end, it is preferable for said fixed housing (210) to have attachment holes (211) penetrating on both sides of the front side and for attachment hooks protruding outward to undergo changes in and restoration of form with tension to selectively attach to the attachment holes of said fixed housing on both sides of the edges on the back.

Moreover, in a peristaltic pump unit (200) comprising components described above, a fixed housing (210) and an attachment housing (220) are similar to a typical peristaltic pump in terms of structure and are equipped with a pressure guide rib (unsigned) with a larger diameter than the outside diameter of the rotary pressure wheel (250) where the outer circumference of the tube (250) is supported closely for the cleaning solution to be guided from one side of the longitudinal direction relative to the tube (250) toward the other side, while the pressure roller (241) exerts pressure on the tube (250) through rotational movement, with the tube (250) wrapped around the circumference of the rotary pressure wheel (240).

Meanwhile, in an automatic medical device cleaning agent supply device according to the present invention, it is important that it is easy to distinguish when said on/off switch (111) is pressed on.

Accordingly, said on/off switch (111) is provided as a round button type that comes with strip-type LED lamps along the circumference of the button area that turn on when the switch is turned on.

Also, it is preferable for said foot switch (400) in an automatic medical device cleaning agent supply device according to the present invention to comprise a switch connection jack (150) and a connection jack (410) wherein the male and female are applied in alternation for interconnection on one end of the power cable (420) and characterized by the inclusion of a foothold (430) connected to the other end of said power cable (420).

Figure 4:
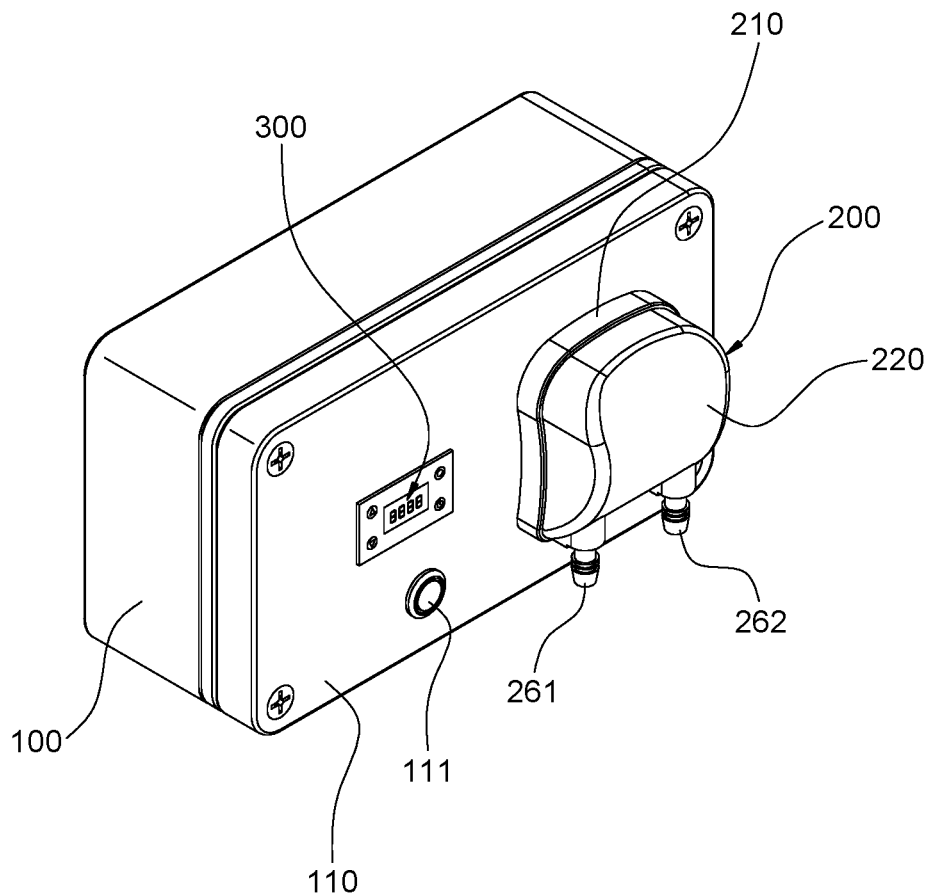
FIG. 4 is a perspective view of an automatic medical device cleaning agent supply device according to the present invention.

FIG. 4 is a perspective view of an automatic medical device cleaning agent supply device according to another embodiment of the present invention.

In the case of the embodiment shown in FIG. 4, the only difference from the embodiment described in reference to FIGS. 1 to 3 is the structure of the timer unit (300), and thus detailed descriptions of components with the same codes will be omitted hereunder.

In an automatic medical device cleaning agent supply device according to another embodiment of the present invention, as shown in FIG. 4, a timer unit (300), which is a part of the device, may be provided as a digital type wherein the operating time is set by touching the buttons on a display.

That is, in the case of said timer unit (300), it is possible to set the time more precisely by providing a digital timer unit wherein the time can be set by touching the buttons on the display.

According to an automatic medical device cleaning agent supply device according to the present invention comprising components described above, it comprises a case, peristaltic pump unit, timer unit, foot switch, and controller that can supply a cleaning agent in relation to the amount of water in the cleaning tank in an easy and automatic way when the cleaning solution is to be supplied to the cleaning tank for cleaning medical devices simply with the pressing and lifting movements of the foot.

Moreover, it comprises a case, peristaltic pump unit, timer unit, foot switch and controller, provided that a structure wherein an attachment housing is secured on a fixed housing in the peristaltic pump unit in a detachable manner for the attachment housing to be selectively detached to facilitate tube replacement and use, through which the tube, which is a consumable, can be replaced conveniently to ensure the ease of maintenance of the device.

Although specific embodiments of the present invention have been described in detail above, the present invention is not limited thereto, and the present invention may be carried out with diverse modifications by a person with ordinary skill in the art to which the present invention pertains and such modifications are included in the scope of the present invention.

What is claimed is:

1. An automatic medical device cleaning agent supply device comprising a case (100), wherein suction tubing (11) and discharge tubing (21) are connected and installed to suction a cleaning solution from a cleaning solution tank (10) via the suction tubing and automatically supply a certain amount of the cleaning solution over a certain amount of time to a cleaning tank containing a certain amount of water via the discharge tubing, wherein an open top is enclosed by a cover (110), which comprises a power connector (130) and a switch connection jack (150) on one side of the case to be supplied power from an external source and operate the device at certain intervals, and wherein an on/off switch (111) is installed in the center of the bottom center of the front of the cover (110); a peristaltic pump unit (200) that is installed inside said case (100) and protrudes externally from the front of said cover (110), to which the suction tubing (11) is connected to one side of the bottom of the exposed portion of the peristaltic pump unit (200), to which the discharge tubing (21) is connected opposite the suction tubing (11) on the bottom of the exposed portion of the peristaltic pump unit (200), and which suctions the cleaning solution from the cleaning solution tank (10) via the suction tubing (11) as a result of rotational operation and discharges a certain amount of the cleaning solution over a certain amount of time into the cleaning tank (20) via the discharge tubing (21); a timer unit (300), which is installed above the on/off switch (111) with respect to the front side of said cover (110) and operates for a preset amount of time in relation to the operation of the peristaltic pump unit (200) to have a certain amount of the cleaning solution be discharged into the cleaning tank (20) over a certain amount time; a foot switch (400), which is selectively connected to the switch connection jack (150) installed on said case (100), wherein the peristaltic pump unit (200) is selectively operated with the pressing and lifting movements of a foot, and which discharges a certain amount of the cleaning solution over a certain amount of time preset using the timer unit (300); and a controller installed inside said case (100) for controlling operation of said peristaltic pump unit (200), timer unit (300), and foot switch unit (400);

wherein said peristaltic pump unit (200) comprises a fixed housing (210) that is fixed in place on one side of the front of the cover (110) to facilitate tube replacement and device maintenance by enhancing the ease of replacing and using tubes and wherein an attachment hole (211) is formed on each side of the front of fixed housing (210);

an attachment housing (220) that is attached and fixed to the front part of the fixed housing (210) wherein attachment hooks (221) that protrude outward undergo changes in and restoration of form with tension to selectively attach to the attachment holes (211) of said fixed housing (210) on both sides of the edges on the back of the attachment housing (220);

a motor (230), which is fixed in place inside the case (100) and to which a connector (233) is connected to an axial tip, with the connector (233) passing through the front of the cover (110) and placed at the center inside the fixed housing (210);

a rotary pressure wheel (240) provided as a wheel of a certain diameter, wherein multiple pressure rollers (241) are fixed in place on the outer surface at regular intervals along the circumference and which are connected by the coupling of protruding and hole parts for the wheel to rotate with the connector (233), the central part on the back side of which is connected to the axial tip of the motor (230);

a tube (250) connected to a suction tubing connection nipple (261) and discharge tubing connection nipple (262) installed for one end and the other end to pass through the bottom of the fixed housing (210) and the attachment housing (220) on one side and the other side, while enclosing the outer circumference of said pressure wheel (240), that suctions the cleaning solution via the suction tubing (11) connected to the suction tubing connection nipple (261) to be discharged via the discharge tubing (21) connected to the discharge tubing connection nipple (262);

and said on/off switch (111) enabling distinction when it is pressed on that comes with lamps along the circumference of the button area that turn on when the switch is turned on.

2. The automatic medical device cleaning agent supply device according to claim 1, wherein said foot switch (400) comprises the switch connection jack (150) and a connection jack (410) wherein the male and female are applied in alternation for interconnection on one end of a power cable (420) and characterized by the inclusion of a foothold (430) connected to the other end of said power cable (420).

3. The automatic medical device cleaning agent supply device according to claim 1, wherein said timer unit (300) is analog wherein the operating time is set by manipulating a dial.

4. The automatic medical device cleaning agent supply device according to claim 1, wherein said timer unit (300) is digital wherein the operating time is set by touching buttons on a display.

* * * * *